(12) United States Patent
Zhang et al.

(10) Patent No.: US 10,081,796 B2
(45) Date of Patent: Sep. 25, 2018

(54) NEUTRALIZATION-RESISTANT CDV MUTANTS AND VIRAL VECTORS

(71) Applicant: International AIDS Vaccine Initiative, New York, NY (US)

(72) Inventors: Xinsheng Zhang, New York, NY (US); Olivia Wallace, New York, NY (US); Arban Domi, New York, NY (US); Christopher Parks, New York, NY (US)

(73) Assignee: INTERNATIONAL AIDS VACCINE INITIATIVE, New York, NY (US)

(*) Notice: Subject to any disclaimer, the term of this patent is extended or adjusted under 35 U.S.C. 154(b) by 25 days.

(21) Appl. No.: 14/993,185

(22) Filed: Jan. 12, 2016

(65) Prior Publication Data

US 2016/0201087 A1    Jul. 14, 2016

Related U.S. Application Data

(60) Provisional application No. 62/102,142, filed on Jan. 12, 2015.

(51) Int. Cl.
*C12N 7/00* (2006.01)

(52) U.S. Cl.
CPC ...... *C12N 7/00* (2013.01); *C12N 2750/14121* (2013.01); *C12N 2750/14122* (2013.01); *C12N 2760/18443* (2013.01)

(58) Field of Classification Search
None
See application file for complete search history.

(56) References Cited

U.S. PATENT DOCUMENTS 9,327,137 B2 * 5/2016 Audonnet .............. A61K 39/12

* cited by examiner

*Primary Examiner* — Nicole Kinsey White
(74) *Attorney, Agent, or Firm* — Duane Morris LLP; Thomas J. Kowalski; Deborah L. Lu

(57) ABSTRACT

The present invention relates to novel canine distemper virus (CDV) neutralization-resistant mutants, methods for making the same and uses for vaccine production.

9 Claims, 10 Drawing Sheets

Specification includes a Sequence Listing.

```
                                                                    48
CDV         MHKGIPKSSKTQTHTQQDRPPQPSTEPEETRTSRARHSITSAQRSTHYDP

Mutant CDV  MHKGIPKSSKTQTHTQQDRPPQPSTEPEETRTSRARHSITSAQRSTHSDP
```

FIG. 5

```
         501                                                                                       547
Mutant CDV  D R D V L I E S N L V V L P T Q S F R Y V V A T Y D I S R S D H A I V Y Y V Y D P I R T I S Y
CDV         D R D V L I E S N L V V L P T Q S F R Y V V A T Y D I S R S E H A I V Y Y V Y D P I R T T S Y
MV          D G D V K L S S N L V H L P G Q D L Y Y V V A T Y D T S S H H A V V Y Y V Y S P S R S S S Y
RPV         D D D V K L S S N L V H L P S R N L Q Y V V A T Y D H R V E H A I V Y H Y Y P A G G R F S Y
PPRV        D D D V K I G S N M V V L P T M D R R Y I S A T Y D V S S G E H A I V Y Y Y Y P T G A R S S Y
DMV         D Q D V K L E S N L V V L P T K D F G Y V T A T Y D T S R S E H A V V Y Y V Y D T A R S S S Y
PDV         D D D V L L E S N L V V L P T Q S F E Y V V A T Y D V S R S D H A I V Y Y V Y D P A R T V S Y
```

| N | P | M | F | H | L |

| N | P | M | F | H | L |

NEUTRALIZATION-RESISTANT CDV MUTANTS AND VIRAL VECTORS

RELATED APPLICATIONS AND INCORPORATION BY REFERENCE

This application claims benefit of and priority to U.S. provisional patent application Ser. No. 62/102,142 filed Jan. 12, 2015.

Reference is made to Zhang et al. "Canine distemper virus neutralization activity is low in human serum and it is sensitive to an amino acid substitution in the hemagglutinin protein", Virology. 2015 August; 482:218-24. doi: 10.1016/j.virol.2015.03.035. Epub 2015 Apr. 14.

The foregoing application and publication, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Feb. 15, 2016, is named 43094_01_2034_SL.txt and is 4,599 bytes in size.

FIELD OF THE INVENTION

The present invention relates to novel canine distemper virus (CDV) neutralization-resistant mutants and uses thereof.

BACKGROUND OF THE INVENTION

Canine distemper virus (CDV) is a member of the Morbillivirus genus, which also includes measles virus (MV), rinderpest virus (RPV), peste des petits ruminants virus and morbilliviruses that infect aquatic mammals (Blixenkrone-Moller, 1993; Di Guardo et al., 2005). These related viruses each generally have a restricted natural host range. For example MV infects humans, RPV infects cattle and other even-toed ungulates, and CDV infects a variety of carnivorous animals. However, CDV infection has been observed in monkey colonies indicating that its host range can extend to primates (Qiu et al., 2011; Sakai et al., 2013a), but so far, there is no conclusive evidence linking CDV to human disease in spite of its speculative association to illness of unknown etiology (Rima and Duprex, 2006). Lab-adapted CDV has been injected into humans without causing symptoms of infection suggesting that humans are a non-permissive host for CDV (Hoekenga et al., 1960), which is consistent with recent studies showing that mutations facilitating both entry and replication are needed for CDV to efficiently adapt to human cells (Otsuki et al., 2013; Sakai et al., 2013b). Prevalent MV immunity induced by universal vaccination or natural infections might also play a role in preventing CDV from crossing the human barrier (de Vries et al., 2014). Despite considerable characterization of antigenic and immunological relationships between CDV and MV (Haile et al., 1982; Orvell and Norrby, 1974, 1980; Stephenson and ter Meulen, 1979), CDV neutralizing antibodies (nAbs) in humans have not been extensively investigated.

Morbilliviruses are attractive candidates for development of replication-competent vectors because modified live vaccines (e.g. MV, CDV, and RPV) have proven to be very safe and efficacious (Buczkowski et al., 2014), and promising preclinical results have been generated with a number of experimental vectors (Brandler et al., 2007; Brandler and Tangy, 2008; Despres et al., 2005; Gauvrit et al., 2008; Guerbois et al., 2009; Miest and Cattaneo, 2014; Wang et al., 2012). Morbilliviruses seem particularly relevant for development of replication-competent AIDS vaccine vectors since this genera of viruses replicates in lymphoid tissues like HIV (Draper and Heeney, 2010; Koff et al., 2013; Parks et al., 2013). Pre-existing MV immunity may make the use of MV vectors problematic, and unlike other viral vector systems in which rare serotype viruses can be used as vector alternatives (Mingozzi et al., 2013; Santra et al., 2009), MV has just one serotype. Thus, CDV has been considered as a MV alternative to minimize the effect of widespread anti-MV antibodies (Miest et al., 2011; Zhang et al., 2013b). Because antibodies specific to MV do cross-react with CDV (Appel et al., 1984; de Vries et al., 2014; Rima, 1983; Taylor et al., 1991), it is important to evaluate the prevalence and potency of CDV neutralizing activity in humans.

Citation or identification of any document in this application is not an admission that such document is available as prior art to the present invention.

SUMMARY OF THE INVENTION

Viral vector based delivery of vaccines or therapeutics can be subject to interference from pre-existing anti-vector immunity. To minimize this effect, there is a need to derive viral vector variants that are less sensitive to the interference from pre-existing antibodies. Applicants describe herein serum selection of canine distemper virus (CDV) mutants that are resistant to neutralization by human serum. CDV was cultured in Vero cells in medium supplemented with human serum containing CDV-neutralizing activity and CDV mutants escaping the immune pressure were selected after several rounds of infection. Genomic sequence analysis identified a single amino acid change from tyrosine to aspartic acid in the hemagglutinin (H) protein that conferred neutralization resistance. The mutation is located in a highly conserved receptor-binding region among H proteins of morbilliviruses including measles virus, rinderpest virus, and peste-des petits ruminants virus, implying a common target for morbillivirus vector modification to evade pre-existing immunity.

Most analysis of neutralization escape viral mutants were done using selective pressure applied with monoclonal antibodies. This invention is based on using human serum to select for viral mutants that escape pre-existing neutralizing antibodies in polyclonal human serum. Therefore the neutralization-resistant mutants thus derived may be used to develop human vaccines or therapeutic vectors that are less sensitive to interference from pre-existing immunity in general human population. The mutation identified in the CDV H protein represents a novel target for morbillivirus-based vector modification to evade prevalent crossreactive human antibodies, elicited by measles virus vaccination or infection. The method of selecting antibody escape variants has general applicability to many viral vectors being investigated and developed for vaccine delivery, gene therapy, or as oncolytic agents.

The present invention relates to a non-naturally occurring CDV neutralization-resistant mutant viral vector which may contain and express an exogenous nucleic acid.

In one embodiment, the viral vector may comprise a mutation in a CDV H protein. The mutation may be a Y537D substitution.

In another embodiment, the viral vector may comprise a mutation in a fusion (F) protein. The mutation may be a Y48S substitution.

In another embodiment, the viral vector may comprise a mutation in a large polymerase (L) protein.

In another embodiment, the exogenous nucleic acid may encode a HIV immunogen and methods for eliciting an immune response against HIV. The method may further comprise administering an adjuvant, which may be comprised of an acrylic polymer and Adjuplex.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1. Distribution of MV nAb titers. Negative threshold was defined as the average nAb titer of unvaccinated monkey serum plus 3× standard deviation. Functional negative threshold was ND50 titer 120 since MV ND50 titers lower than that do not prevent measles (Chen et al., 1990). For the 146 volunteers, 90.4% had MV titers higher than 120 and majority of the titers were in ranges of 120.1-1,000 (61.0%) and 1,000-2,000 (16.4%), which correspond to MV antibodies induced by vaccinations (Hussain et al., 2013; Leuridan et al., 2010).

Figure 3:
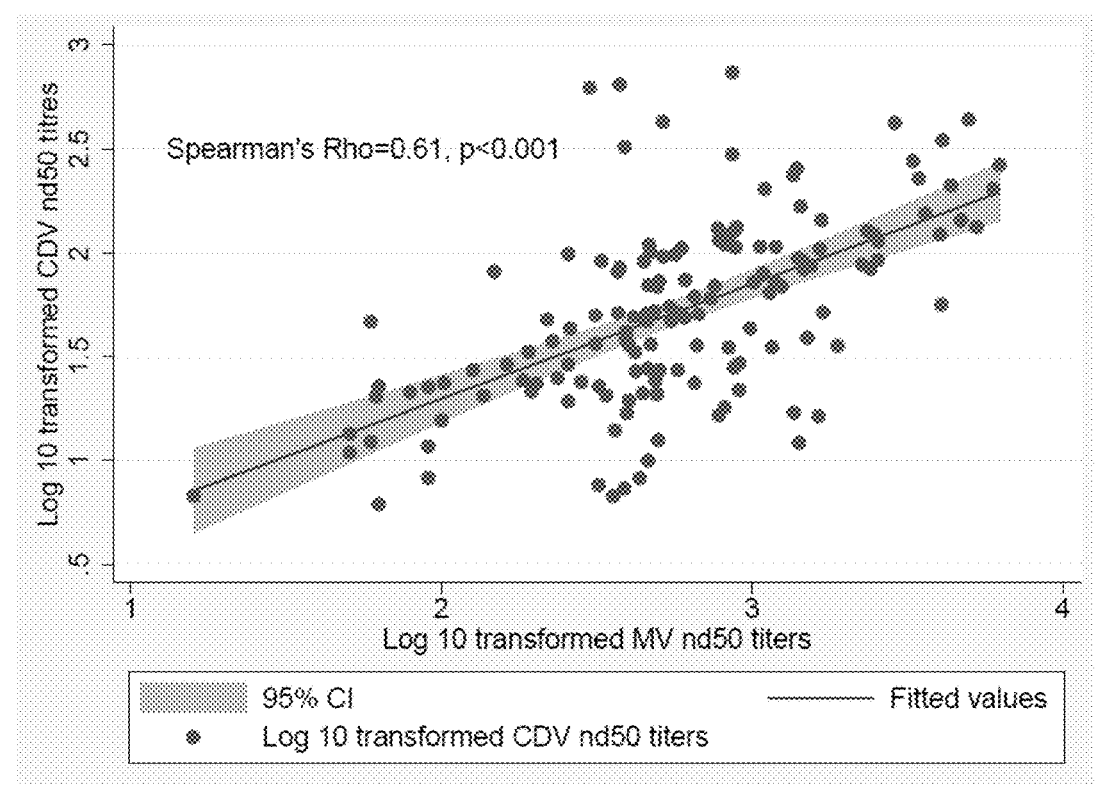

FIG. 3. Strong correlation was found between MV and CDV nAb using Spearman's rank correlation analysis (Spearman's coefficient Rho=0.61, p<0.001) suggesting CDV neutralization is due to cross-reactive MV nAbs that are present at low quantities in the volunteers who had relatively high MV nAb titers. Relationship between Log 10 transformed MV and CDV ND50 titers is shown by the fitted line. The shaded area represented 95% confidence interval of the fitted values.

Figure 4:
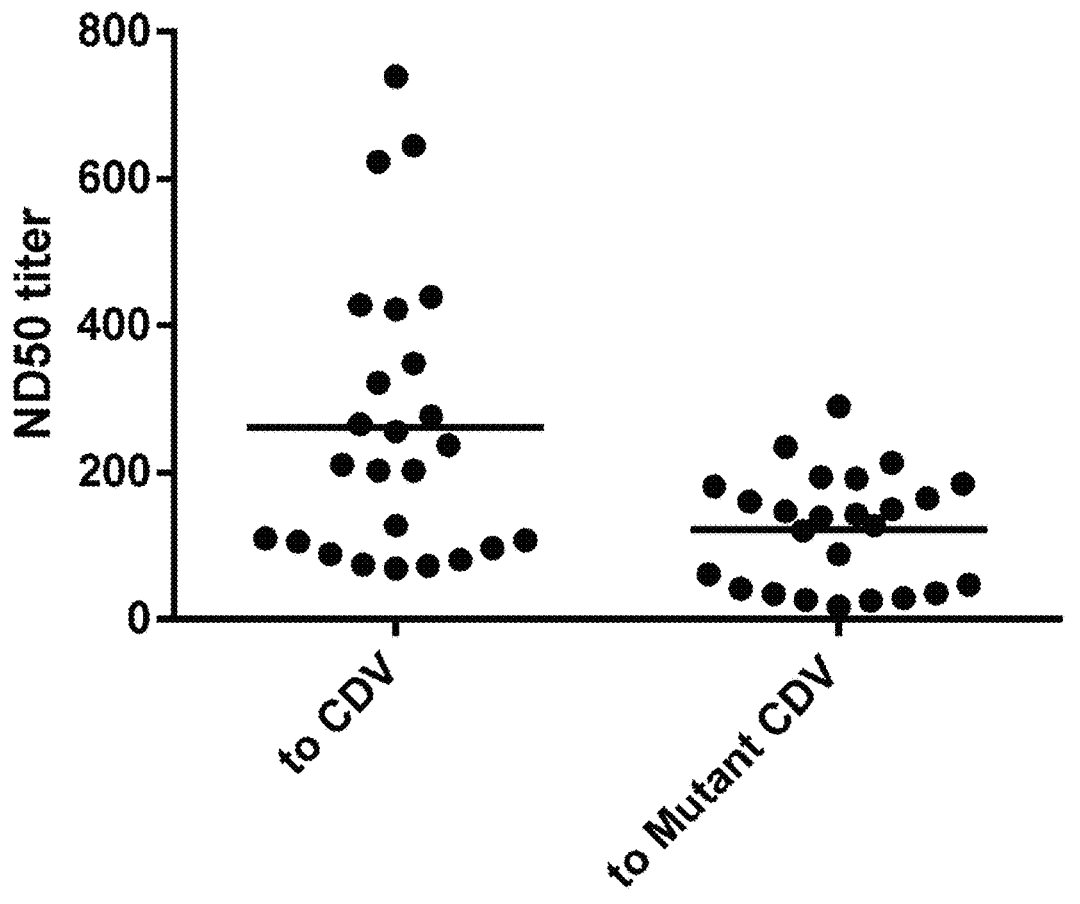

FIG. 4. Comparing the serum neutralizing potency to CDV and the mutant CDV generated by human serum selection. Dots represent 25 serum samples randomly selected from the 146 volunteers. The two bars represented mean ND50 values to each virus. The average ND50 titer to mutant CDV was 2.1 fold lower than that to CDV indicating the mutant CDV was more resistant to neutralization.

FIG. 5. Mutation in F gene of the neutralization escape CDV isolate (SEQ ID NO: 1). A point mutation changed the tyrosine to serine at aa position 48 as highlighted in bold (SEQ ID NO: 2). The mutation locates in signal peptide region of CDV F. The signal peptide is from amino acid 1-135 in precursor F protein (Plattet et al., 2007) and residues 1-50 are shown.

FIG. 6. Alignment of aa 501-547 of CDV H (SEQ ID NO: 4) and corresponding regions in H proteins of MV (SEQ ID NO: 5), rinderpest virus (P09460) (SEQ ID NO: 6), peste des petits ruminants virus (PPRV AHA58209) (SEQ ID NO: 7), dolphin morbillivirus (DMV Q66411) (SEQ ID NO: 8) and phocine distemper virus (PDV P28882) (SEQ ID NO: 9). Amino acid residues conserved among all 6 morbilliviruses are boxed. The CDV H is 607 aa in length and the point mutation changed Y to D at aa position 537 (highlighted in bold) (SEQ ID NO: 3) in H of the neutralization-resistant mutant. This sequence corresponds to aa 505-551 in MV H (Masse et al., 2004), which is involved in H binding to MV receptors and is fully conserved among a variety of MV isolates including Edmonston, Schwarz, Moraten and Zagreb vaccine viruses (H protein sequence accession # in GenBank: P08362, AAA566657, CAL40872, and AM237414, respectively).

FIG. 7. IC50 of the 2F4 antibody. The bars represented concentrations of the 2F4 antibody needed to neutralize 50% of the input CDV or the CDV mutant. The highest dilution of the monoclonal antibody causing 50% neutralization of CDV was 1,017 and calculated IC50 was 1.8 µg/ml based on this dilution. In contrast, the maximal dilution to neutralize 50% of the mutant virus was only 39.7, which was equivalent to IC50 of 46.6 µg/ml, suggesting the Y to D substitution in the receptor binding site of H diminished the antibody binding.

FIGS. 8A-8C. Schematics of genome of recombinant CDVs (rCDV) differing only at aa position 537 in H. To confirm that the H mutation alone is responsible for the neutralization resistance, two rCDVs were created that have either Y (A) or D (B) at aa537 of H for comparing neutralization sensitivity to human serum. The rCDVs were recovered using rescue protocol described previously (Zhang et al., 2013b). The two viruses induced similar CPE (cell rounding, detaching, and fusion pointed by red arrow) on Vero cells typically seen in CDV infections (C).

FIG. 9. ND50 titers of serum against recombinant CDV with original H (rCDVH$^{537Y}$) and rCDV with the Y537D mutation in H (rCDVH$^{Y537D}$). Dots on the left represent 12 serum samples randomly selected from the 146 volunteers and the two lines represented mean ND50 values to each virus. The average ND50 titer to rCDVH$^{Y537D}$ was 3.9 fold lower than that to rCDVH$^{537Y}$, which is consistent with the reduced neutralization sensitivity of mutant CDV derived from the human serum selection, indicating the Y to D mutation alone can cause neutralization resistance.

Figure 10:
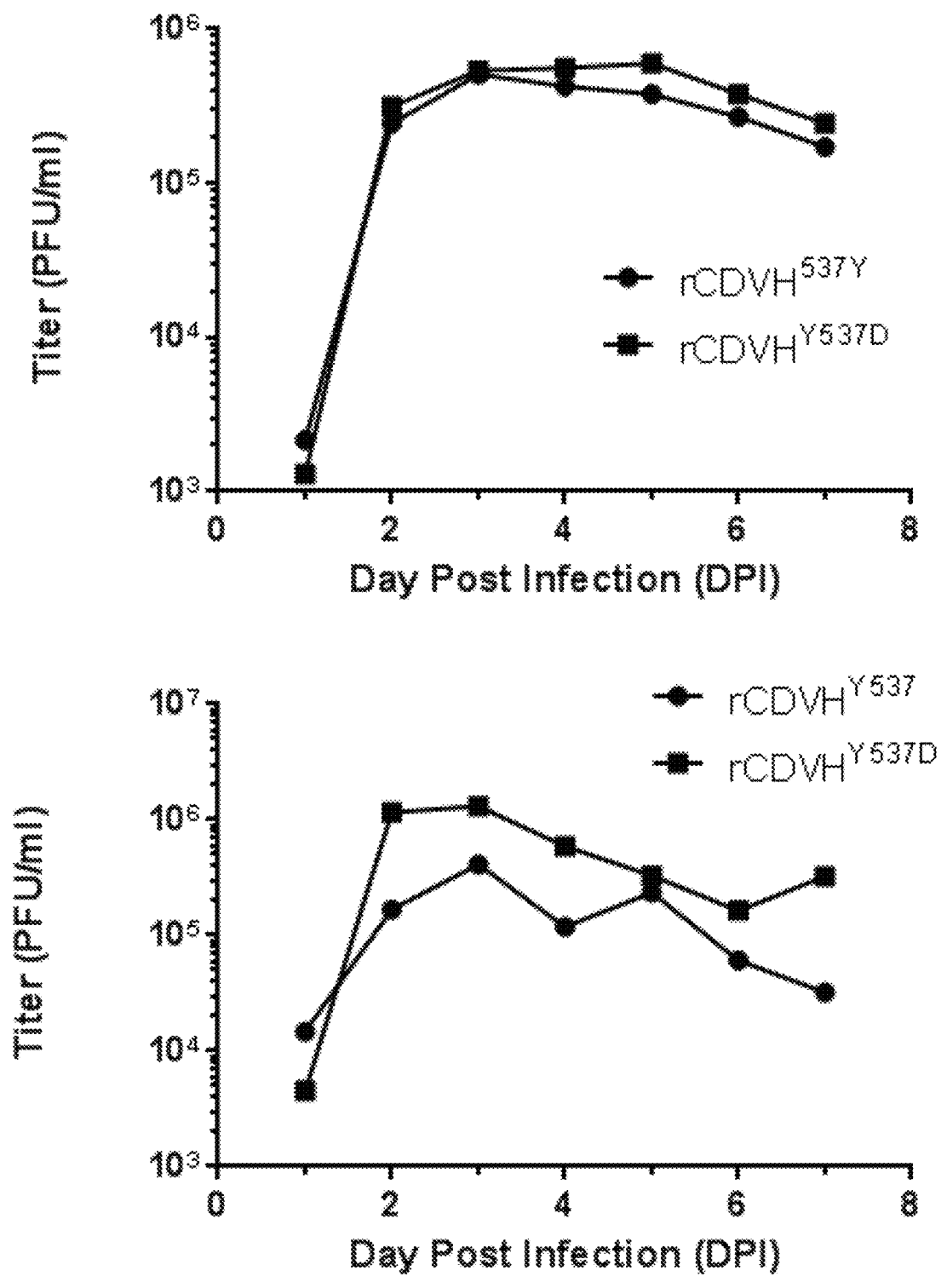

FIG. 10. Growth kinetics of rCDVH537Y and rCDVHy537D on Vero (top) and Vero/dogSLAM (bottom) cells. The two viruses were propagated on either Vero or transgenic Vero cells overexpressing dog SLAM receptor at multiplicity of infection (MOI) of 0.02. Culture supernatants were taken daily from day post infection (DPI) 1 to 7 and plaque forming units (PFU) titers determined on respective cell line for propagation according to previously described protocol (Zhang et al., 2013b). The results represent averages of two independent experiments. Overall rCDVH$^{Y537D}$ grew to slightly higher titers than rCDVH$^{537Y}$ on both cell lines, indicating the Y to D substitution does not compromise viral growth.

DETAILED DESCRIPTION OF THE INVENTION

Figure 2:
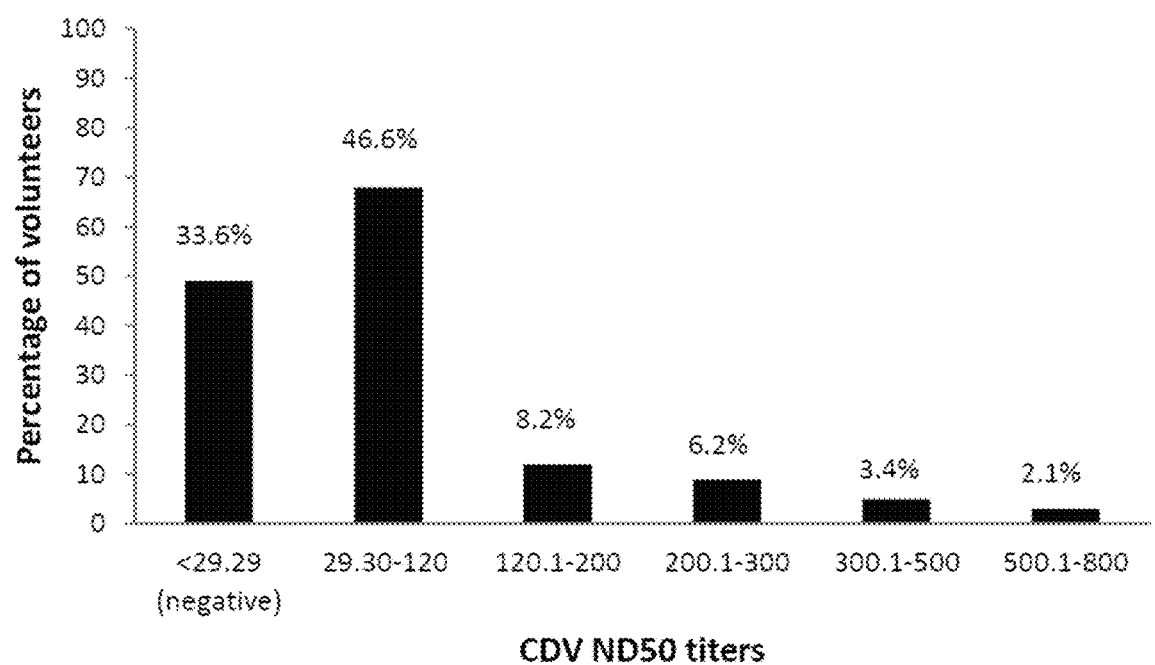
FIG. 2. Distribution of CDV nAb titers. Negative threshold was defined as the average ND50 titer of unvaccinated ferret serum plus 3× standard deviation. Total 80.2% of the volunteers had CDV ND50 titers either below the negative threshold or in 29.30-120 range.

A serosurvey involving 146 healthy adult volunteers in eastern Africa was conducted to evaluate measles virus (MV) and canine distemper virus (CDV) neutralizing antibody (nAb) prevalence and potency. MV plaque reduction neutralization test (PRNT) indicated that all sera were positive for MV nAbs. Furthermore, 50% neutralizing dose (ND50) of a majority of the sera corresponded to antibody levels induced by vaccination. In contrast, CDV nAbs were low and detected in sera with high MV nAb titers. To determine molecular basis of the CDV neutralization, a CDV mutant was generated with increased resistance to neutralization by human serum. Genomic sequence analysis identified 10 mutations, of which four caused nonsynonymous amino acid changes each in fusion (F) and hemagglutinin (H) and two in large polymerase (L) proteins. The H substitution occurred in a conserved region among morbilliviruses involved in receptor interactions, and may imply a common H target for morbillivirus antibody cross-neutralization.

In this invention, 146 serum samples collected from healthy adults in three eastern Africa countries were surveyed for both MV and CDV nAbs. Applicants found that MV nAbs were prevalent in these samples and the frequency of samples with significant CDV nAb titers was low. Moreover, when CDV neutralizing activity was detected, it correlated with high anti-MV titers. Applicants also used antiserum to derive an in vitro escape mutant CDV with increased resistance to neutralization by human serum. Genomic sequence analysis of the resistant strain revealed an amino acid substitution in a conserved region of the MV and CDV hemagglutinin (H) proteins that may help design H variants that are less sensitive to the effect of anti-vector immunity.

Results from this study showed that anti-CDV neutralizing activity was relatively low or absent in sera from African clinical trial volunteers. To Applicants' knowledge, this is the first human serosurvey involving a large number of volunteers conducted to investigate the prevalence and potency of CDV nAbs. The results also indicated that CDV neutralizing activity likely was related to cross-reactive MV-specific antibodies. Applicants analyzed a smaller number of American serum samples obtained from a commercial source and found their CDV neutralization potency was similarly low (data not shown). CDV nAbs have been reported before, for example in serum from subacute sclerosing panencephalitis (SSPE) patients and in a small number of human samples, which were shown to weakly neutralize a MV-CDV chimeric virus (Miest et al., 2011; Sato et al., 1973), but these studies were not designed to estimate the prevalence of anti-CDV neutralization. Applicants' serosurvey results indicate that low level CDV nAbs can exist in a significant proportion of human populations probably induced by MV vaccination or infection. This contrasts with data from dogs, mice, and non-human primates vaccinated with live MV or vectors expressing MV F and H proteins in which detectable CDV nAbs were not elicited although vaccination prevented infection or disease progression following pathogenic CDV challenge (Appel et al., 1984; de Vries et al., 2014; Taylor et al., 1991; Wild et al., 1993). Thus, it seems to suggest that MV induces antibodies that can cross-neutralize CDV in humans, but less frequently in experimentally infected animals. Among the 146 volunteers in the survey, 66.4% were positive for low CDV nAbs. This frequency of positivity suggests that MV vaccination or MV infection is the likely inducer of the CDV nAbs, although responses induced by CDV exposure cannot be ruled out. Among the 5 CRCs in the survey, samples from the Masaka CRC had the highest CDV nAb titers. This may be related to the rural location of the Masaka site compared with the other 4 CRC locations. It is conceivable that rural locality could increase the risk of human CDV exposure due to a presence of unvaccinated domestic dogs and wild animal species that are occasionally infected by CDV during distemper outbreaks (Guiserix et al., 2007; Leisewitz et al., 2001; van de Bildt et al., 2002).

The results showed that MV nAbs are prevalent since MV ND50 titers are all above the positive cutoff value of 8.63 that was calculated based on average titers of a negative monkey serum sample. In another study where PRNT was used for analysis of clinical human samples, a titer of 8 was found to be the threshold for detecting low levels of nAbs (Ratnam et al., 1995), which is similar to Applicants' cutoff value. Although all of the samples Applicants analyzed were positive for MV antibodies, 9.6% had ND50 titers lower than 120, which is the threshold for prevention of illness due to measles virus infection (Chen et al., 1990). If Applicants assume that CDV ND50 titers greater than 120 are needed to inhibit infection with a vector based on CDV, then 80.2% of the African volunteers were below this threshold.

Two amino acid substitutions were identified in the glycoproteins and two in the L protein of the CDV mutant that was selected for increased resistance to serum neutralization. Because the membrane glycoproteins F and H are the only known targets of nAbs (Orvell and Norrby, 1974, 1980), the L mutations likely did not contribute to neutralization resistance. H gene diversity is common and often implicated in CDV evolution driven by immunologic pressure (Martella et al., 2006; Sekulin et al., 2011; Trebbien et al., 2014). The F amino acid substitution is located in the signal peptide that is present in the precursor protein but absent in mature form, and therefore it is less likely to affect neutralization resistance (Plattet et al., 2007; von Messling et al., 2004). The Y537 substitution in H is located in a region that is conserved among morbilliviruses and corresponds to amino acid Y541 in MV H, which is a contact residue involved in binding to cellular CD46 and Nectin and is in a domain associated with antibody neutralization (Mateo et al., 2013; Santiago et al., 2010; Tahara et al., 2013; Zhang et al., 2013a). Due to high sequence identity in this H region, it is likely that nAbs induced by MV vaccination will bind the same domain in CDV H and Applicants' data suggest that the Y to D substitution may have modified an epitope recognized by some cross-reactive nAbs in human serum. It was evident that the Y537D substitution did not abolish neutralization activity in human serum indicating that there were other binding sites recognized by nAbs, which is consistent with polyclonal nature of human antiserum against MV (Santibanez et al., 2005; Santibanez et al., 2002).

CDV H mutants (such as, but not limited to, a CDV with a Y537D substitution) are useful for development of vaccine vectors or oncolytic agents that are less subject to effects of pre-existing MV-specific antibodies. Additional characterization of the mutant H is required to determine if the Y537D substitution is stable during CDV propagation without selective pressure, if the substitution is attenuating, and whether it alters receptor specificity. The general approach used to select the H mutant resistant to human serum may also be valuable for developing new glycoproteins for vector development particularly in cases like CDV where an animal virus is being developed for use as a human vaccine vector or oncolytic agent.

CDV glycoproteins can also be modified for developing novel vaccine or oncolytic vectors with altered cell specificity. CDV enters host cells through attachment of H to specific cell receptors and subsequent F-mediated fusion of viral envelope and cell membrane. Wild-type CDV isolates primarily target signaling lymphocyte activation molecule (SLAM) and nectin-4 positive cells while vaccine strains of CDV gain broader cell tropisms besides recognizing these two receptors (ref 1: The morbillivirus receptor SLAM (CD150). Tatsuo H, Yanagi Y. Microbiol Immunol. 2002; 46(3):135-42. Ref 2: Dog nectin-4 is an epithelial cell receptor for canine distemper virus that facilitates virus entry and syncytia formation. Noyce R S, Delpeut S, Richardson C D. Virology. 2013 Feb. 5; 436(1):210-20). Therefore, cell tropisms of CDV vectors differ depending on usage of wild-type or vaccine CDV H proteins. In addition, extra specificity determinants can be added to H protein ectodomain for specific cancer cell targeting and natural receptor interactions deactivated by H mutations, which has been developed in MV-based oncolytic vector research (ref: Paramyxovirus entry and targeted vectors for cancer therapy. Cattaneo R, PLoS Pathog. 2010 Jun. 24; 6(6)). Cell retargeting can also be achieved through F modifications. Because F function is activated after protease cleavage, paramyxovirus vectors including MV and Sendai virus can be modified to retarget cancer cells through cancer-specific cleavage of F (ref 1: Generation of a recombinant Sendai virus that is selectively activated and lyses human tumor cells expressing matrix metalloproteinases. Kinoh H, Inoue M, Washizawa K, Yamamoto T, Fujikawa S, et al. Gene Ther. 2004; 11:1137-1145. Ref 2: Oncolytic efficacy and enhanced safety of measles virus activated by tumor-secreted matrix metalloproteinases. Springfeld C, von Messling V, Frenzke M, Ungerechts G, Buchholz C J, Cattaneo R. Cancer Res. 2006; 66:7694-7700). CDV polymerase protein L has genome transcription and replication functions. Modifications in L of vaccine or oncolytic CDV vectors can change viral replication ability, which can serve as a tool to modulate level of CDV attenuation (ref: Development of a challenge-protective vaccine concept by modification of the viral RNA-dependent RNA polymerase of canine distemper virus. Silin D, Lyubomska O, Ludlow M, Duprex W P, Rima B K. J Virol. 2007 December; 81(24): 13649-58).

In one embodiment, the present invention encompasses the use of immunogens expressed in recombinant CDV vectors, advantageously as HIV-1 vaccine components.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, F(ab')$_2$, Fv and scFv which are capable of binding the epitope determinant. These antibody fragments retain some ability to selectively bind with its antigen or receptor and include, for example:

Fab, the fragment which contains a monovalent antigen-binding fragment of an antibody molecule can be produced by digestion of whole antibody with the enzyme papain to yield an intact light chain and a portion of one heavy chain;

Fab', the fragment of an antibody molecule can be obtained by treating whole antibody with pepsin, followed by reduction, to yield an intact light chain and a portion of the heavy chain; two Fab' fragments are obtained per antibody molecule;

F(ab')$_2$, the fragment of the antibody that can be obtained by treating whole antibody with the enzyme pepsin without subsequent reduction; F(ab')$_2$ is a dimer of two Fab' fragments held together by two disulfide bonds;

scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

A "neutralizing antibody" may inhibit the entry of HIV-1 virus F with a neutralization index >1.5 or >2.0. Broad and potent neutralizing antibodies may neutralize greater than about 50% of HIV-1 viruses (from diverse clades and different strains within a clade) in a neutralization assay. The inhibitory concentration of the monoclonal antibody may be less than about 25 mg/ml to neutralize about 50% of the input virus in the neutralization assay.

It should be understood that the proteins, including the antibodies and/or antigens of the invention may differ from the exact sequences illustrated and described herein. Thus, the invention contemplates deletions, additions and substitutions to the sequences shown, so long as the sequences function in accordance with the methods of the invention. In this regard, particularly preferred substitutions are generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may be used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention can readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies and/or antigens of the present invention may be used in accordance with the present invention. In certain embodiments, the antigens and/or antibodies of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the antigens and/or antibodies in vitro and/or in cultured cells may be used.

For applications where it is desired that the antibodies and/or antigens be expressed in vivo, for example when the transgenes of the invention are used in DNA or DNA-containing vaccines, any vector that allows for the expression of the antibodies and/or antigens of the present invention and is safe for use in vivo may be used. In preferred embodiments the vectors used are safe for use in humans, mammals and/or laboratory animals.

For the antibodies and/or antigens of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The present invention relates to a recombinant vector expressing a foreign epitope. Advantageously, the epitope is an HIV epitope. In an advantageous embodiment, the HIV epitope is a soluble envelope glycoprotein, however, the present invention may encompass additional HIV antigens, epitopes or immunogens. Advantageously, the HIV epitope is an HIV antigen, HIV epitope or an HIV immunogen, such as, but not limited to, the HIV antigens, HIV epitopes or HIV immunogens of U.S. Pat. Nos. 7,341,731; 7,335,364; 7,329,807; 7,323,553; 7,320,859; 7,311,920; 7,306,798; 7,285,646; 7,285,289; 7,285,271; 7,282,364; 7,273,695; 7,270,997; 7,262,270; 7,244,819; 7,244,575; 7,232,567; 7,232,566; 7,223,844; 7,223,739; 7,223,534; 7,223,368; 7,220,554; 7,214,530; 7,211,659; 7,211,432; 7,205,159; 7,198,934; 7,195,768; 7,192,555; 7,189,826; 7,189,522; 7,186,507; 7,179,645; 7,175,843; 7,172,761; 7,169,550; 7,157,083; 7,153,509; 7,147,862; 7,141,550; 7,129,219; 7,122,188; 7,118,859; 7,118,855; 7,118,751; 7,118,742; 7,105,655; 7,101,552; 7,097,971; 7,097,842; 7,094,405; 7,091,049; 7,090,648; 7,087,377; 7,083,787; 7,070,787; 7,070,781; 7,060,273; 7,056,521; 7,056,519; 7,049,136; 7,048,929; 7,033,593; 7,030,094; 7,022,326; 7,009,037; 7,008,622; 7,001,759; 6,997,863; 6,995,008; 6,979,535; 6,974,574; 6,972,126; 6,969,609; 6,964,769; 6,964,762; 6,958,158; 6,956,059; 6,953,689; 6,951,648; 6,946,075; 6,927,031; 6,919,319; 6,919,318; 6,919,077; 6,913,752; 6,911,315; 6,908,617; 6,908,612; 6,902,743; 6,900,010; 6,893,869; 6,884,785; 6,884,435; 6,875,435; 6,867,005; 6,861,234; 6,855,539; 6,841,381 6,841,345; 6,838,477; 6,821,955; 6,818,392; 6,818,222; 6,815,217; 6,815,201; 6,812,026; 6,812,025; 6,812,024; 6,808,923; 6,806,055; 6,803,231; 6,800,613; 6,800,288; 6,797,811; 6,780,967; 6,780,598; 6,773,920; 6,764,682; 6,761,893; 6,753,015; 6,750,005; 6,737,239; 6,737,067; 6,730,304; 6,720,310; 6,716,823; 6,713,301; 6,713,070; 6,706,859; 6,699,722; 6,699,656; 6,696,291; 6,692,745; 6,670,181; 6,670,115; 6,664,406; 6,657,055; 6,657,050; 6,656,471; 6,653,066; 6,649,409; 6,649,372; 6,645,732; 6,641,816; 6,635,469; 6,613,530; 6,605,427; 6,602,709; 6,602,705; 6,600,023; 6,596,477; 6,596,172; 6,593,103; 6,593,079; 6,579,673; 6,576,758; 6,573,245; 6,573,040; 6,569,418; 6,569,340; 6,562,800; 6,558,961; 6,551,828; 6,551,824; 6,548,275; 6,544,780; 6,544,752; 6,544,728; 6,534,482; 6,534,312; 6,534,064; 6,531,572; 6,531,313; 6,525,179; 6,525,028; 6,524,582; 6,521,449; 6,518,030; 6,518,015; 6,514,691; 6,514,503; 6,511,845; 6,511,812; 6,511,801; 6,509,313; 6,506,384; 6,503,882; 6,495,676; 6,495,526; 6,495,347; 6,492,123; 6,489,131; 6,489,129; 6,482,614; 6,479,286; 6,479,284; 6,465,634; 6,461,615; 6,458,560; 6,458,527; 6,458,370; 6,451,601; 6,451,592; 6,451,323; 6,436,407; 6,432,633; 6,428,970; 6,428,952; 6,428,790; 6,420,139; 6,416,997; 6,410,318; 6,410,028; 6,410,014; 6,407,221; 6,406,710; 6,403,092; 6,399,295; 6,392,013; 6,391,657; 6,384,198; 6,380,170; 6,376,170; 6,372,426; 6,365,187; 6,358,739; 6,355,248; 6,355,247; 6,348,450; 6,342,372; 6,342,228; 6,338,952; 6,337,179; 6,335,183; 6,335,017; 6,331,404; 6,329,202; 6,329,173; 6,328,976; 6,322,964; 6,319,666; 6,319,665; 6,319,500; 6,319,494; 6,316,205; 6,316,003; 6,309,633; 6,306,625; 6,296,807; 6,294,322; 6,291,239; 6,291,157; 6,287,568; 6,284,456; 6,284,194; 6,274,337; 6,270,956; 6,270,769; 6,268,484; 6,265,562; 6,265,149; 6,262,029; 6,261,762; 6,261,571; 6,261,569; 6,258,599; 6,258,358; 6,248,332; 6,245,331; 6,242,461; 6,241,986; 6,235,526; 6,235,466; 6,232,120; 6,228,361; 6,221,579; 6,214,862; 6,214,804; 6,210,963; 6,210,873; 6,207,185; 6,203,974; 6,197,755; 6,197,531; 6,197,496; 6,194,142; 6,190,871; 6,190,666; 6,168,923; 6,156,302; 6,153,408; 6,153,393; 6,153,392; 6,153,378; 6,153,377; 6,146,635; 6,146,614; 6,143,876 6,140,059; 6,140,043; 6,139,746; 6,132,992; 6,124,306; 6,124,132; 6,121,006; 6,120,990; 6,114,507; 6,114,143; 6,110,466; 6,107,020; 6,103,521; 6,100,234; 6,099,848; 6,099,847; 6,096,291; 6,093,405; 6,090,392; 6,087,476; 6,083,903; 6,080,846; 6,080,725;

6,074,650; 6,074,646; 6,070,126; 6,063,905; 6,063,564; 6,060,256; 6,060,064; 6,048,530; 6,045,788; 6,043,347; 6,043,248; 6,042,831; 6,037,165; 6,033,672; 6,030,772; 6,030,770; 6,030,618; 6,025,141; 6,025,125; 6,020,468; 6,019,979; 6,017,543; 6,017,537; 6,015,694; 6,015,661; 6,013,484; 6,013,432; 6,007,838; 6,004,811; 6,004,807; 6,004,763; 5,998,132; 5,993,819; 5,989,806; 5,985,926; 5,985,641; 5,985,545; 5,981,537; 5,981,505; 5,981,170; 5,976,551; 5,972,339; 5,965,371; 5,962,428; 5,962,318; 5,961,979; 5,961,970; 5,958,765; 5,958,422; 5,955,647; 5,955,342; 5,951,986; 5,951,975; 5,942,237; 5,939,277; 5,939,074; 5,935,580; 5,928,930; 5,928,913; 5,928,644; 5,928,642; 5,925,513; 5,922,550; 5,922,325; 5,919,458; 5,916,806; 5,916,563; 5,914,395; 5,914,109; 5,912,338; 5,912,176; 5,912,170; 5,906,936; 5,895,650; 5,891,623; 5,888,726; 5,885,580 5,885,578; 5,879,685; 5,876,731; 5,876,716; 5,874,226; 5,872,012; 5,871,747; 5,869,058; 5,866,694; 5,866,341; 5,866,320; 5,866,319; 5,866,137; 5,861,290; 5,858,740; 5,858,647; 5,858,646; 5,858,369; 5,858,368; 5,858,366; 5,856,185; 5,854,400; 5,853,736; 5,853,725; 5,853,724; 5,852,186; 5,851,829; 5,851,529; 5,849,475; 5,849,288; 5,843,728; 5,843,723; 5,843,640; 5,843,635; 5,840,480; 5,837,510; 5,837,250; 5,837,242; 5,834,599; 5,834,441; 5,834,429; 5,834,256; 5,830,876; 5,830,641; 5,830,475; 5,830,458; 5,830,457; 5,827,749; 5,827,723; 5,824,497; 5,824,304; 5,821,047; 5,817,767; 5,817,754; 5,817,637; 5,817,470; 5,817,318; 5,814,482; 5,807,707; 5,804,604; 5,804,371; 5,800,822; 5,795,955; 5,795,743; 5,795,572; 5,789,388; 5,780,279; 5,780,038; 5,776,703; 5,773,260; 5,770,572; 5,766,844; 5,766,842; 5,766,625; 5,763,574; 5,763,190; 5,762,965; 5,759,769; 5,756,666; 5,753,258; 5,750,373; 5,747,641; 5,747,526; 5,747,028; 5,736,320; 5,736,146; 5,733,760; 5,731,189; 5,728,385; 5,721,095; 5,716,826; 5,716,637; 5,716,613; 5,714,374; 5,709,879; 5,709,860; 5,709,843; 5,705,331; 5,703,057; 5,702,707 5,698,178; 5,688,914; 5,686,078; 5,681,831; 5,679,784; 5,674,984; 5,672,472; 5,667,964; 5,667,783; 5,665,536; 5,665,355; 5,660,990; 5,658,745; 5,658,569; 5,643,756; 5,641,624; 5,639,854; 5,639,598; 5,637,677; 5,637,455; 5,633,234; 5,629,153; 5,627,025; 5,622,705; 5,614,413; 5,610,035; 5,607,831; 5,606,026; 5,601,819; 5,597,688; 5,593,972; 5,591,829; 5,591,823; 5,589,466; 5,587,285; 5,585,254; 5,585,250; 5,580,773; 5,580,739; 5,580,563; 5,573,916; 5,571,667; 5,569,468; 5,558,865; 5,556,745; 5,550,052; 5,543,328; 5,541,100; 5,541,057; 5,534,406; 5,529,765; 5,523,232; 5,516,895; 5,514,541; 5,510,264; 5,500,161; 5,480,967; 5,480,966; 5,470,701; 5,468,606; 5,462,852; 5,459,127; 5,449,601; 5,447,838; 5,447,837; 5,439,809; 5,439,792; 5,418,136; 5,399,501; 5,397,695; 5,391,479; 5,384,240; 5,374,519; 5,374,518; 5,374,516; 5,364,933; 5,359,046; 5,356,772; 5,354,654; 5,344,755; 5,335,673; 5,332,567; 5,320,940; 5,317,009; 5,312,902; 5,304,466; 5,296,347; 5,286,852; 5,268,265; 5,264,356; 5,264,342; 5,260,308; 5,256,767; 5,256,561; 5,252,556; 5,230,998; 5,230,887; 5,227,159; 5,225,347; 5,221,610 5,217,861; 5,208,321; 5,206,136; 5,198,346; 5,185,147; 5,178,865; 5,173,400; 5,173,399; 5,166,050; 5,156,951; 5,135,864; 5,122,446; 5,120,662; 5,103,836; 5,100,777; 5,100,662; 5,093,230; 5,077,284; 5,070,010; 5,068,174; 5,066,782; 5,055,391; 5,043,262; 5,039,604; 5,039,522; 5,030,718; 5,030,555; 5,030,449; 5,019,387; 5,013,556; 5,008,183; 5,004,697; 4,997,772; 4,983,529; 4,983,387; 4,965,069; 4,945,082; 4,921,787; 4,918,166; 4,900,548; 4,888,290; 4,886,742; 4,885,235; 4,870,003; 4,869,903; 4,861,707; 4,853,326; 4,839,288; 4,833,072 and 4,795,739.

In another embodiment, HIV, or immunogenic fragments thereof, may be utilized as the HIV epitope. For example, the HIV nucleotides of U.S. Pat. Nos. 7,393,949, 7,374,877, 7,306,901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any epitope recognized by an HIV antibody may be used in the present invention. For example, the anti-HIV antibodies of U.S. Pat. Nos. 6,949,337, 6,900,010, 6,821,744, 6,768,004, 6,613,743, 6,534,312, 6,511,830, 6,489,131, 6,242,197, 6,114,143, 6,074,646, 6,063,564, 6,060,254, 5,919,457, 5,916,806, 5,871,732, 5,824,304, 5,773,247, 5,736,320, 5,637,455, 5,587,285, 5,514,541, 5,317,009, 4,983,529, 4,886,742, 4,870,003 and 4,795,739 are useful for the present invention. Furthermore, monoclonal anti-HIV antibodies of U.S. Pat. Nos. 7,074,556, 7,074,554, 7,070,787, 7,060,273, 7,045,130, 7,033,593, RE39,057, 7,008,622, 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

The vectors used in accordance with the present invention should typically be chosen such that they contain a suitable gene regulatory region, such as a promoter or enhancer, such that the antigens and/or antibodies of the invention can be expressed.

For example, when the aim is to express the antibodies and/or antigens of the invention in vitro, or in cultured cells, or in any prokaryotic or eukaryotic system for the purpose of producing the protein(s) encoded by that antibody and/or antigen, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the antibodies and/or antigens under the identified circumstances.

When the aim is to express the antibodies and/or antigens of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies and/or antigens of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Sendai virus vectors are preferred. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors. Such viruses are also contemplated for the expression of the herein disclosed proteins, such as EnvF and EnvG.

The nucleotide sequences and vectors of the invention can be delivered to cells, for example if aim is to express and the HIV-1 antigens in cells in order to produce and isolate the expressed proteins, such as from cells grown in culture. For expressing the antibodies and/or antigens in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies and/or antigens can be carried out in any suitable type of host cells, such as bacterial cells, yeast, insect cells, and mammalian cells. The antibodies and/or antigens of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

In preferred embodiments, the nucleotide sequences, antibodies and/or antigens of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, antibodies and/or antigens of the invention are preferably administered as a component of an immunogenic composition comprising the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies and/or antigens of the invention to a subject, such as a human, such that the antibodies and/or antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri (caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., AlK(SO$_4$)$_2$, AlNa (SO$_4$)$_2$, AlNH(SO$_4$)$_2$, silica, alum, Al(OH)$_3$, Ca$_3$(PO$_4$)$_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34$^{th}$ Annual Meeting of the German Society of Immunology; Lingnau, K. et al (2002) Vaccine 20(29-30): 3498-508), JUVAVAX™ (U.S. Pat. No. 6,693,086), certain natural substances (e.g., wax D from *Mycobacterium tuberculosis*, substances found in *Cornyebacterium parvum, Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A. M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or α-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate expression vectors.

In an advantageous embodiment, the adjuvants may be lecithin combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)).

The immunogenic compositions can be designed to introduce the nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

A specific embodiment of the invention provides methods of inducing an immune response against HIV in a subject by administering an immunogenic composition of the invention, preferably comprising an adenovirus vector containing DNA encoding one or more of the epitopes of the invention, one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which can be administered as a protein, on a plasmid (e.g., pTHr.HIVA) or in a viral vector (e.g., MVA. HIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject comprises administering at least one priming dose of an HIV immunogen and at least one boosting dose of an HIV immunogen, wherein the immunogen in each dose can be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 2-6 or more weeks.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Results

MV nAbs in African Serum Samples:

Serum was collected from 146 healthy adult male and female volunteers between 19 and 50 years of age (Table 1). The volunteers were participants in vaccine trial preparedness cohorts (Kamali, 2014) enrolled at 5 clinical research centers (CRCs) supported by IAVI in Kenya (Kilifi and Nairobi), Rwanda (Kigali), and Uganda (Masaka and Entebbe).

Figure 1:
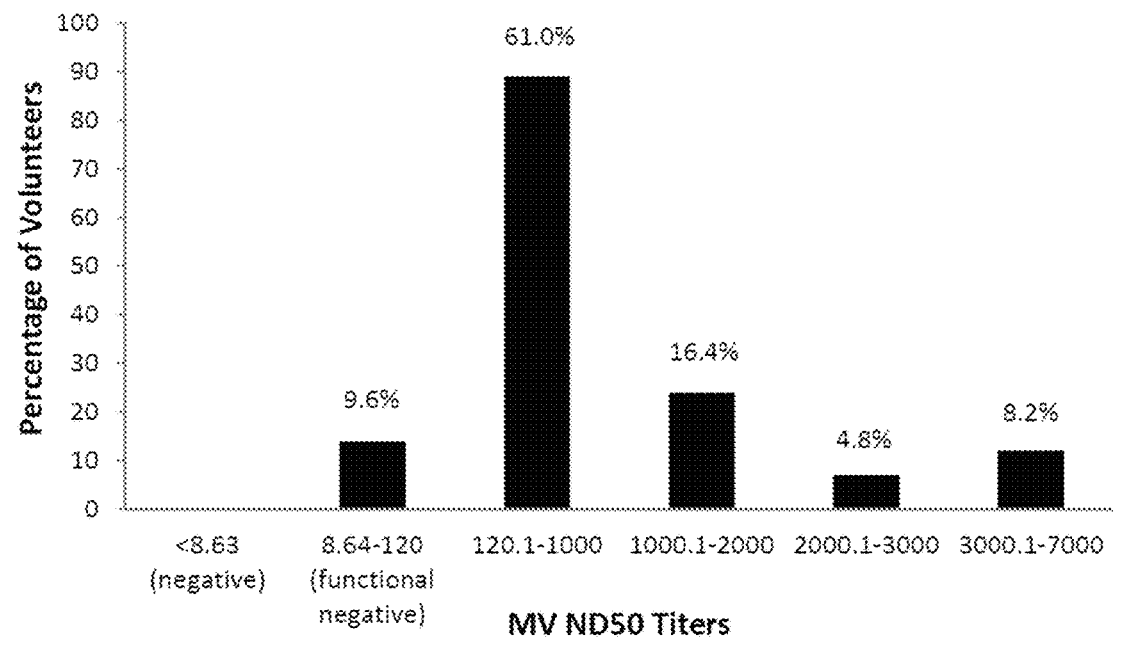

The threshold for MV nAb positivity was defined as average ND50 titer of naïve macaque serum plus 3 times standard deviation. When the PRNT was performed with the naïve macaque serum control, the threshold was calculated as 8.63. All serum samples from African volunteers were positive for MV nAbs since their titers were above this threshold (FIG. 1) and the ND50 values ranged from 16.0 to 6,270. For comparison, serum from a monkey vaccinated against MV had an ND50 value of 1,446 and earlier studies in college students indicated that ND50 titers below 120 do not prevent measles (Chen et al., 1990). Overall, 77.4% of the African serum ND50 values fell between 120-2,000, which is approximately equivalent to 300-5,000 milli-International Unit (mIU) of WHO international standard MV antibodies (Cohen et al., 2007). The 300-5,000 mIU range is consistent with MV nAb levels induced by routine vaccination (Hussain et al., 2013; Leuridan et al., 2010), suggesting that these volunteers probably were vaccinated, although an MV vaccination history was not available to confirm this. Thirteen percent of the samples exhibited MV ND50 titers above 2,000, which was indicative of a stronger response than typically observed after vaccination suggesting that some volunteers had contracted measles at some point (Leuridan et al., 2010). No significant difference in ND50 titers was observed across gender or age groups. Overall antibody titers were similar among the regions except for Nairobi where volunteers exhibited significantly lower titers than other regions ($p=0.01$).

Generally low CDV nAbs titers in African serum samples and their correlation with the magnitude of MV nAbs:

When the PRNT was performed with naïve ferret serum, the average CDV ND50 titer plus 3 times standard deviation was determined to be 29.29, which Applicants employed as Applicants' threshold for positivity. Based on this, approximately 33.6% of the African volunteer serum samples were negative. ND50 titers in 46.6% of the volunteers were between 29.3-120 (FIG. 2) and the remaining 19.8% had CDV ND50 titers above 120 but below 800. For comparison, serum from a ferret recently vaccinated with live-attenuated CDV was 33,551. Similar to MV nAbs, CDV ND50 titers were not significantly different across gender and age. With the exception of the volunteers from the Masaka CRC where higher CDV nAbs ($p<0.001$) were detected, no significant difference was observed for the other geographical regions. Although the CDV nAb titers overall were low, positive CDV nAb values generally correlated with higher magnitude MV titers (FIG. 3, Spearman's $\rho=0.61$, $p<0.001$). Given the lack of epidemiologic evidence to support frequent infection of CDV in humans, this result suggests that CDV neutralization is due to cross-neutralizing MV antibodies, which are present in low quantities and are detectable with the PRNT only in volunteers with relatively high MV ND50 titers.

A mutant CDV was generated that was more resistant to neutralization by human serum:

To better understand the molecular basis of the cross-neutralization, a neutralization-resistant CDV mutant was isolated and its genomic nucleotide sequence determined. The neutralization-resistant CDV mutant was selected using a single healthy adult donor serum of American origin that was available from a commercial source and had detectable CDV and MV nAbs. The neutralization-resistant CDV mutant grew in Vero cells with similar kinetics as the progenitor virus (data not shown) indicating that the escape mutation(s) had little effect on replication in culture. When the mutant was analyzed with the PRNT using 25 serum samples randomly selected from the African volunteers, it was more resistant to neutralization in all sera tested. Across the 25 samples, the ND50 titer determined with the mutant virus was decreased by 2.1 fold compared to the progenitor CDV (FIG. 4).

Genomic sequence analysis was performed on the resistant virus population and 10 nucleotide substitutions were detected. Five of the substitutions were in protein coding sequences but were silent in terms of amino acid coding and one mutation was detected in the trailer region (Table 2). Four mutations caused amino acid coding changes with one in the fusion (F), one in the H and two in the large polymerase (L) proteins. The F gene mutation resulted in a tyrosine (Y) to serine (S) substitution at amino acid (aa) 48 in the signal peptide (FIG. 5), while the H mutation resulted in a Y to aspartic acid (D) substitution at aa537 (FIG. 6). The H amino acid substitution occurred in a region that is involved in virus receptor interactions and is conserved across morbilliviruses (FIG. 6).

Example 2: Materials and Methods

Cell and Virus:

Vero cells were used in the CDV or MV plaque reduction neutralization test (PRNT). The cells were maintained in Dulbecco's modified Eagle's medium (DMEM, Gibco) supplemented with 10% fetal bovine serum. The CDV used was a clonal isolate derived from a commercial vaccine (Schering-Plough, USA) prepared with the live-attenuated Onderstepoort virus. Isolation and culture of the CDV mutant are described below. Neutralization sensitivity of the mutant CDV was assessed with a subset of the human serum samples. MV used in these studies was an attenuated Edmonston strain derived from a commercial vaccine preparation (ATTENUVAX, MERCK & CO., USA). All three viruses were propagated in Vero cells and plaque forming units (PFU) were quantified as described previously for CDV (Zhang et al., 2013b).

Serum Samples:

A total of 146 human serum samples were analyzed with the CDV and MV PRNT. These samples were collected from three eastern African countries from healthy adults, ages 19 to 50, enrolled in vaccine-trial preparatory studies to determine regional HIV incidence (Kamali, 2014). For CDV PRNT, sera from naïve and CDV-vaccinated ferrets served as negative and positive controls. Naïve and MV-vaccinated monkey sera were used for MV PRNT controls. All serum samples were inactivated at 56° C. for 30 min before conducting the PRNT.

CDV and MV PRNT:

The PRNT was conducted with CDV, mutant CDV, or MV according to a standard MV PRNT protocol with slight modifications (Cohen et al., 2007). Notably, infections were performed using Vero monolayers instead of infecting cells in suspension. Briefly, four-fold serial dilutions were made with each serum sample starting with a 1:4 dilution made by mixing 12.5 ul of serum with 37.5 ul of DMEM in duplicate wells in 96-well plates. The next dilution was made by transferring 12.5 ul of the diluted serum samples to 37.5 ul of DMEM and so on. To each well of diluted serum, an equal volume (37.5 ul) of CDV or MV solution was added and incubated for 2 h. Thus, the first serum dilution on the plate was 1:8. For each experiment, either ferret or monkey sera were used as negative and positive controls and were processed in the same way as test samples. Vero cell monolayers were prepared one day before in 24-well plates and were approximately 80% confluent the following day when they were fed with 0.2 ml of fresh medium. After mixtures of virus and diluted serum were incubated for 2 h to allow antibody binding, the suspension (50 ul) was transferred from the 96-well plates to the 24-well plates containing Vero cell monolayers. Following 2 hour virus adsorption, the medium was removed and cells were fed with 1 ml DMEM containing 0.75% methylcellulose. Three days later, medium was removed and cells were washed once with PBS and then fixed with 100% cold methanol for 30 min. For viral plaque detection, the cells were incubated with a rabbit antiserum specific for CDV nucleoprotein or a commercial monoclonal antibody specific for MV nucleoprotein (AbCAM, USA). After removing the primary antibody, incubation was conducted with anti-rabbit or anti-mouse secondary antibodies conjugated with horse-radish peroxidase (HRP). Staining was performed by addition of 3-Amino-9-ethylcarbazole (AEC) substrate for HRP (Sigma). Average plaque numbers were calculated from the duplicated wells at every dilution for each serum sample. For determining neutralization titers, the assay was standardized to generate about 30 plaques per well when virus was treated without serum. At least four identical wells were infected with the virus only for generating an average plaque number in each experiment. Fifty percent neutralization dose (ND50) titers were defined as the reciprocal of the serum dilution at which the number of plaques is reduced to 50% relative to virus only controls. The calculation of ND50 titers followed the Karber formula as described for MV PRNT (Cohen et al., 2007). The serum samples were considered positive for CDV or MV nAbs if the titers were greater than the average ND50 titer of the respective naïve ferret or monkey serum plus 3 times the standard deviation.

Selection of Neutralization Escape Mutants Using Human Immune Serum:

Neutralization resistant CDV was isolated using a commercial human serum prepared from a single healthy adult donor in USA (Innovative Research, USA). The serum sample was positive for both MV and CDV neutralizing antibodies. The commercial human serum was used because there was sufficient quantity available to conduct serial virus passage in the presence of nAbs, and this also allowed Applicants to preserve limited quantities of serum from the African volunteers. For selecting CDV mutants that resisted neutralization, $1 \times 10^6$ PFU of CDV in 1 ml of culture medium was incubated with 200 μl of the undiluted serum in 37° C. incubator for 1 h, after which the virus was added to a Vero cell monolayer cultured in T25 flask (Nunc, USA). After 1 h adsorption, the virus inoculum was replaced with 5 ml of cell culture growth medium that was supplemented with 5% human immune serum. Medium supernatant was harvested 6 days later and 20% was used to infect a fresh monolayer that was subsequently incubated in medium containing 5% human immune serum. The supernatant was harvested when cytopathic effect (CPE) appeared. Virus passage in the presence of human serum was repeated 2 more times. After the 4th round of infection, virus was analyzed with the PRNT using a subset of the African serum samples. The genomes of parental and mutant CDV were sequenced and compared.

Analysis of CDV Genomic Nucleotide Sequences:

Genomic sequences were determined by extracting RNA from infected cell lysates, performing reverse transcription and PCR (RT-PCR) using primers based on the CDV nucleotide sequence in GenBank (accession number AF014953), and performing DNA sequencing on amplified DNA fragments. Overlapping sequences were assembled and anylyzed using Vector NTI (version 11.5, Life Technologies). Genomic sequences from CDV and the neutralization-resistant mutant were aligned with ClustalW program in Lasergene software (DNASTAR Inc.).

Statistical Analysis:

Data analyses were conducted using Stata (v13.1, College Station, Tex., USA). Spearman's rank correlation analyses were performed to determine the relationship between CDV and MV nAb titers. Spearman's correlation coefficient Rho and P values were given. The titers were transformed to Log 10 expression for the correlation analyses and linear regression shown in FIG. 3.

Example 3: Tables

TABLE 1

Demographic characteristics of volunteers involved in the study (n = 146). CRC: Clinical Research Center.

| CRC | Total | Volunteer sex | | | | Volunteer age | | | |
|---|---|---|---|---|---|---|---|---|---|
| | | Male | | Female | | | | | |
| | | N | % | N | % | Median | Mean | Min | Max |
| Kigali | 30 | 14 | 46.7 | 16 | 53.3 | 27.5 | 30.2 | 20 | 50 |
| Masaka | 30 | 20 | 66.7 | 10 | 33.3 | 36.5 | 36.7 | 23 | 48 |
| Kilifi | 26 | 13 | 50.0 | 13 | 50.0 | 32.5 | 32.2 | 20 | 46 |
| Nairobi | 30 | 17 | 56.7 | 13 | 43.3 | 26.5 | 29.0 | 20 | 41 |
| Entebbe | 30 | 15 | 50.0 | 15 | 50.0 | 30.5 | 30.1 | 19 | 45 |
| Total | 146 | 79 | 54.1 | 67 | 45.9 | 32.0 | 31.6 | 19 | 50 |

TABLE 2

Summary of nucleotide changes and amino acid substitutions between the CDV and neutralization resistant CDV mutant.

Nucleotide differences between CDV and the neutralization resistant CDV[a]

| nt[b] | CDV | Mutant CDV | aa substitution[c] |
|---|---|---|---|
| M gene nt 3,432-4,439 | | | |
| 3,665 | A | G | Silent |
| 3,707 | A | G | Silent |
| 3,710 | A | G | Silent |

TABLE 2-continued

Summary of nucleotide changes and amino acid substitutions between the CDV and neutralization resistant CDV mutant.
Nucleotide differences between CDV and the neutralization resistant CDV[a]

| nt[b] | CDV | Mutant CDV | aa substitution[c] |
|---|---|---|---|
| F gene nt 4,935-6,923 | | | |
| 5,077 | A | C | Y to S |
| H gene nt 7,079-8,902 | | | |
| 7,786 | T | A | Silent |
| 8,687 | T | G | Y to D |
| L gene nt 9,030-15,584 | | | |
| 11,455 | A | G | Q to R |
| 14,298 | A | G | I to V |
| 14,324 | C | T | Silent |
| Trailer nt 15,585-15,690 | | | |
| 15,591 | A | G | N/A |

[a]Genomic cDNA sequences of the two viruses were compared. Uniform length of 15,690 nt was achieved for each genomic cDNA after trimming sequence ends and assembly.
[b]Nucleotide locations of genes and positions for nt changes in each gene are shown.
[c]Amino acid coding substitutions caused by the nt changes are shown for each gene Example 4: References Appel, M. J., Shek, W. R., Shesberadaran, H., Norrby, E., 1984. Measles virus and inactivated canine distemper virus induce incomplete immunity to canine distemper. Archives of virology 82, 73-82.

Blixenkrone-Moller, M., 1993. Biological properties of phocine distemper virus and canine distemper virus. APMIS. Supplementum 36, 1-51.

Brandler, S., Lucas-Hourani, M., Moris, A., Frenkiel, M. P., Combredet, C., Fevrier, M., Bedouelle, H., Schwartz, O., Despres, P., Tangy, F., 2007. Pediatric measles vaccine expressing a dengue antigen induces durable serotype-specific neutralizing antibodies to dengue virus. PLoS neglected tropical diseases 1, e96.

Brandler, S., Tangy, F., 2008. Recombinant vector derived from live attenuated measles virus: potential for flavivirus vaccines. Comparative immunology, microbiology and infectious diseases 31, 271-291.

Buczkowski, H., Muniraju, M., Parida, S., Banyard, A. C., 2014. Morbillivirus vaccines: Recent successes and future hopes. Vaccine 32, 3155-3161.

Chen, R. T., Markowitz, L. E., Albrecht, P., Stewart, J. A., Mofenson, L. M., Preblud, S. R., Orenstein, W. A., 1990. Measles antibody: reevaluation of protective titers. The Journal of infectious diseases 162, 1036-1042.

Cohen, B. J., Audet, S., Andrews, N., Beeler, J., test, W.H.O.w.g.o.m.p.r.n., 2007. Plaque reduction neutralization test for measles antibodies: Description of a standardised laboratory method for use in immunogenicity studies of aerosol vaccination. Vaccine 26, 59-66.

de Vries, R. D., Ludlow, M., Verburgh, R. J., van Amerongen, G., Yuksel, S., Nguyen, D. T., McQuaid, S., Osterhaus, A. D., Duprex, W. P., de Swart, R. L., 2014. Measles Vaccination of Non-Human Primates Provides Partial Protection against Infection with Canine Distemper Virus. Journal of virology.

Despres, P., Combredet, C., Frenkiel, M. P., Lorin, C., Brahic, M., Tangy, F., 2005. Live measles vaccine expressing the secreted form of the West Nile virus envelope glycoprotein protects against West Nile virus encephalitis. The Journal of infectious diseases 191, 207-214.

Di Guardo, G., Marruchella, G., Agrimi, U., Kennedy, S., 2005. Morbillivirus infections in aquatic mammals: a brief overview. Journal of veterinary medicine. A, Physiology, pathology, clinical medicine 52, 88-93.

Draper, S. J., Heeney, J. L., 2010. Viruses as vaccine vectors for infectious diseases and cancer. Nature reviews. Microbiology 8, 62-73.

Gauvrit, A., Brandler, S., Sapede-Peroz, C., Boisgerault, N., Tangy, F., Gregoire, M., 2008. Measles virus induces oncolysis of mesothelioma cells and allows dendritic cells to cross-prime tumor-specific CD8 response. Cancer research 68, 4882-4892.

Guerbois, M., Moris, A., Combredet, C., Najburg, V., Ruffie, C., Fevrier, M., Cayet, N., Brandler, S., Schwartz, O., Tangy, F., 2009. Live attenuated measles vaccine expressing HIV-1 Gag virus like particles covered with gp160DeltaV1V2 is strongly immunogenic. Virology 388, 191-203.

Guiserix, M., Bahi-Jaber, N., Fouchet, D., Sauvage, F., Pontier, D., 2007. The canine distemper epidemic in Serengeti: are lions victims of a new highly virulent canine distemper virus strain, or is pathogen circulation stochasticity to blame? Journal of the Royal Society, Interface/the Royal Society 4, 1127-1134.

Haile, R., Smith, P., Read, D., Nassim, D., Warlow, C., Russell, W. C., 1982. A study of measles virus and canine distemper virus antibodies, and of childhood infections in multiple sclerosis patients and controls. Journal of the neurological sciences 56, 1-10.

Hoekenga, M. T., Schwarz, A. J., Carrizo Palma, H., Boyer, P. A., 1960. Experimental vaccination against measles. II. Tests of live measles and live distemper vaccine in human volunteers during a measles epidemic in Panama. Journal of the American Medical Association 173, 868-872.

Hussain, H., Akram, D. S., Chandir, S., Khan, A. J., Memon, A., Halsey, N. A., 2013. Immune response to 1 and 2 dose regimens of Measles vaccine in Pakistani children. Human vaccines & immunotherapeutics 9.

Kamali, A. P., M. A.; Lakhi, S.; Karita, E.; Inambao, M.; Sanders, E. J.; Anzala, O.; Latka, M. H.; Bekker, L. G.; Kaleebu, P.; Asiki, G.; Ssetaala, A.; Ruzagira, E.; Allen, S.; Farmer, P.; Hunter, E., Mutua, G.; Makkan, H.; Tichacek, A.; Brill, I. K.; Fast, P.; Stevens, G.; Chetty, P.; Amornkul, P. N.; Gilmour, J.; and The IAVI Africa HIV Prevention Partnership, 2014. Creating an African HIV Clinical Research and Prevention Trials Network: HIV Prevalence, Incidence and Transmission. PloS one (in review).

Koff, W. C., Burton, D. R., Johnson, P. R., Walker, B. D., King, C. R., Nabel, G. J., Ahmed, R., Bhan, M. K., Plotkin, S. A., 2013. Accelerating next-generation vaccine development for global disease prevention. Science 340, 1232910.

Leisewitz, A. L., Carter, A., van Vuuren, M., van Blerk, L., 2001. Canine distemper infections, with special reference to South Africa, with a review of the literature. Journal of the South African Veterinary Association 72, 127-136.

Leuridan, E., Hens, N., Hutse, V., Ieven, M., Aerts, M., Van Damme, P., 2010. Early waning of maternal measles antibodies in era of measles elimination: longitudinal study. Bmj 340, c1626.

Martella, V., Cirone, F., Elia, G., Lorusso, E., Decaro, N., Campolo, M., Desario, C., Lucente, M. S., Bellacicco, A. L., Blixenkrone-Moller, M., Carmichael, L. E., Buonavoglia, C., 2006. Heterogeneity within the hemagglutinin genes of canine distemper virus (CDV) strains detected in Italy. Veterinary microbiology 116, 301-309.

Masse, N., Ainouze, M., Neel, B., Wild, T. F., Buckland, R., Langedijk, J. P., 2004. Measles virus (MV) hemagglutinin: evidence that attachment sites for MV receptors SLAM and CD46 overlap on the globular head. Journal of virology 78, 9051-9063.

Mateo, M., Navaratnarajah, C. K., Syed, S., Cattaneo, R., 2013. The measles virus hemagglutinin beta-propeller head beta4-beta5 hydrophobic groove governs functional interactions with nectin-4 and CD46 but not those with the signaling lymphocytic activation molecule. Journal of virology 87, 9208-9216.

Miest, T. S., Cattaneo, R., 2014. New viruses for cancer therapy: meeting clinical needs. Nature reviews. Microbiology 12, 23-34.

Miest, T. S., Yaiw, K. C., Frenzke, M., Lampe, J., Hudacek, A. W., Springfeld, C., von Messling, V., Ungerechts, G., Cattaneo, R., 2011. Envelope-chimeric entry-targeted measles virus escapes neutralization and achieves oncolysis. Molecular therapy: the journal of the American Society of Gene Therapy 19, 1813-1820.

Mingozzi, F., Chen, Y., Edmonson, S. C., Zhou, S., Thurlings, R. M., Tak, P. P., High, K. A., Vervoordeldonk, M. J., 2013. Prevalence and pharmacological modulation of humoral immunity to AAV vectors in gene transfer to synovial tissue. Gene therapy 20, 417-424.

Orvell, C., Norrby, E., 1974. Further studies on the immunologic relationships among measles, distemper, and rinderpest viruses. Journal of immunology 113, 1850-1858.

Orvell, C., Norrby, E., 1980. Immunological relationships between homologous structural polypeptides of measles and canine distemper virus. The Journal of general virology 50, 231-245.

Otsuki, N., Nakatsu, Y., Kubota, T., Sekizuka, T., Seki, F., Sakai, K., Kuroda, M., Yamaguchi, R., Takeda, M., 2013. The v protein of canine distemper virus is required for virus replication in human epithelial cells. PloS one 8, e82343.

Parks, C. L., Picker, L. J., King, C. R., 2013. Development of replication-competent viral vectors for HIV vaccine delivery. Current opinion in HIV and AIDS 8, 402-411.

Plattet, P., Cherpillod, P., Wiener, D., Zipperle, L., Vandevelde, M., Wittek, R., Zurbriggen, A., 2007. Signal peptide and helical bundle domains of virulent canine distemper virus fusion protein restrict fusogenicity. Journal of virology 81, 11413-11425.

Qiu, W., Zheng, Y., Zhang, S., Fan, Q., Liu, H., Zhang, F., Wang, W., Liao, G., Hu, R., 2011. Canine distemper outbreak in rhesus monkeys, China. Emerging infectious diseases 17, 1541-1543.

Ratnam, S., Gadag, V., West, R., Burris, J., Oates, E., Stead, F., Bouilianne, N., 1995. Comparison of commercial enzyme immunoassay kits with plaque reduction neutralization test for detection of measles virus antibody. Journal of clinical microbiology 33, 811-815.

Rima, B. K., 1983. The proteins of morbilliviruses. The Journal of general virology 64 (Pt 6), 1205-1219.

Rima, B. K., Duprex, W. P., 2006. Morbilliviruses and human disease. The Journal of pathology 208, 199-214.

Sakai, K., Nagata, N., Ami, Y., Seki, F., Suzaki, Y., Iwata-Yoshikawa, N., Suzuki, T., Fukushi, S., Mizutani, T., Yoshikawa, T., Otsuki, N., Kurane, I., Komase, K., Yamaguchi, R., Hasegawa, H., Saijo, M., Takeda, M., Morikawa, S., 2013a. Lethal canine distemper virus outbreak in cynomolgus monkeys in Japan in 2008. Journal of virology 87, 1105-1114.

Sakai, K., Yoshikawa, T., Seki, F., Fukushi, S., Tahara, M., Nagata, N., Ami, Y., Mizutani, T., Kurane, I., Yamaguchi, R., Hasegawa, H., Saijo, M., Komase, K., Morikawa, S., Takeda, M., 2013b. Canine distemper virus associated with a lethal outbreak in monkeys can readily adapt to use human receptors. Journal of virology 87, 7170-7175.

Santiago, C., Celma, M. L., Stehle, T., Casasnovas, J. M., 2010. Structure of the measles virus hemagglutinin bound to the CD46 receptor. Nature structural & molecular biology 17, 124-129.

Santibanez, S., Niewiesk, S., Heider, A., Schneider-Schaulies, J., Berbers, G. A., Zimmermann, A., Halenius, A., Wolbert, A., Deitemeier, I., Tischer, A., Hengel, H., 2005. Probing neutralizing-antibody responses against emerging measles viruses (MVs): immune selection of MV by H protein-specific antibodies? The Journal of general virology 86, 365-374.

Santibanez, S., Tischer, A., Heider, A., Siedler, A., Hengel, H., 2002. Rapid replacement of endemic measles virus genotypes. The Journal of general virology 83, 2699-2708.

Santra, S., Sun, Y., Korioth-Schmitz, B., Fitzgerald, J., Charbonneau, C., Santos, G., Seaman, M. S., Ratcliffe, S. J., Montefiori, D. C., Nabel, G. J., Ertl, H. C., Letvin, N. L., 2009. Heterologous prime/boost immunizations of rhesus monkeys using chimpanzee adenovirus vectors. Vaccine 27, 5837-5845.

Sato, T. A., Yamanouchi, K., Shishido, A., 1973. Presence of neutralizing antibody to canine distemper virus in sera of patients with subacute sclerosing panencephalitis. Archiv fur die gesamte Virusforschung 42, 36-41.

Sekulin, K., Hafner-Marx, A., Kolodziejek, J., Janik, D., Schmidt, P., Nowotny, N., 2011. Emergence of canine distemper in Bavarian wildlife associated with a specific amino acid exchange in the haemagglutinin protein. Veterinary journal 187, 399-401.

Stephenson, J. R., ter Meulen, V., 1979. Antigenic relationships between measles and canine distemper viruses: comparison of immune response in animals and humans to individual virus-specific polypeptides. Proceedings of the National Academy of Sciences of the United States of America 76, 6601-6605.

Tahara, M., Ohno, S., Sakai, K., Ito, Y., Fukuhara, H., Komase, K., Brindley, M. A., Rota, P. A., Plemper, R. K., Maenaka, K., Takeda, M., 2013. The receptor-binding site of the measles virus hemagglutinin protein itself constitutes a conserved neutralizing epitope. Journal of virology 87, 3583-3586.

Taylor, J., Pincus, S., Tartaglia, J., Richardson, C., Alkhatib, G., Briedis, D., Appel, M., Norton, E., Paoletti, E., 1991. Vaccinia virus recombinants expressing either the measles virus fusion or hemagglutinin glycoprotein protect dogs against canine distemper virus challenge. Journal of virology 65, 4263-4274.

Trebbien, R., Chriel, M., Struve, T., Hjulsager, C. K., Larsen, G., Larsen, L. E., 2014. Wildlife reservoirs of canine distemper virus resulted in a major outbreak in Danish farmed mink (Neovison vison). PloS one 9, e85598.

van de Bildt, M. W., Kuiken, T., Visee, A. M., Lema, S., Fitzjohn, T. R., Osterhaus, A. D., 2002. Distemper outbreak and its effect on African wild dog conservation. Emerging infectious diseases 8, 211-213.

von Messling, V., Milosevic, D., Devaux, P., Cattaneo, R., 2004. Canine distemper virus and measles virus fusion glycoprotein trimers: partial membrane-proximal ectodomain cleavage enhances function. Journal of virology 78, 7894-7903.

Wang, X., Feng, N., Ge, J., Shuai, L., Peng, L., Gao, Y., Yang, S., Xia, X., Bu, Z., 2012. Recombinant canine distemper virus serves as bivalent live vaccine against rabies and canine distemper. Vaccine 30, 5067-5072.

Wild, T. F., Bernard, A., Spehner, D., Villeval, D., Drillien, R., 1993. Vaccination of mice against canine distemper virus-induced encephalitis with vaccinia virus recombinants encoding measles or canine distemper virus antigens. Vaccine 11, 438-444.

Zhang, X., Lu, G., Qi, J., Li, Y., He, Y., Xu, X., Shi, J., Zhang, C. W., Yan, J., Gao, G. F., 2013a. Structure of measles virus hemagglutinin bound to its epithelial receptor nectin-4. Nature structural & molecular biology 20, 67-72.

Zhang, X., Wallace, O., Wright, K. J., Backer, M., Coleman, J. W., Koehnke, R., Frenk, E., Domi, A., Chiuchiolo, M. J., DeStefano, J., Narpala, S., Powell, R., Morrow, G., Boggiano, C., Zamb, T. J., Richter King, C., Parks, C. L., 2013b. Membrane-bound SIV envelope trimers are immunogenic in ferrets after intranasal vaccination with a replication-competent canine distemper virus vector. Virology 446, 25-36.

Example 5: Neutralization Resistant CDV Mutant

Figure 7:
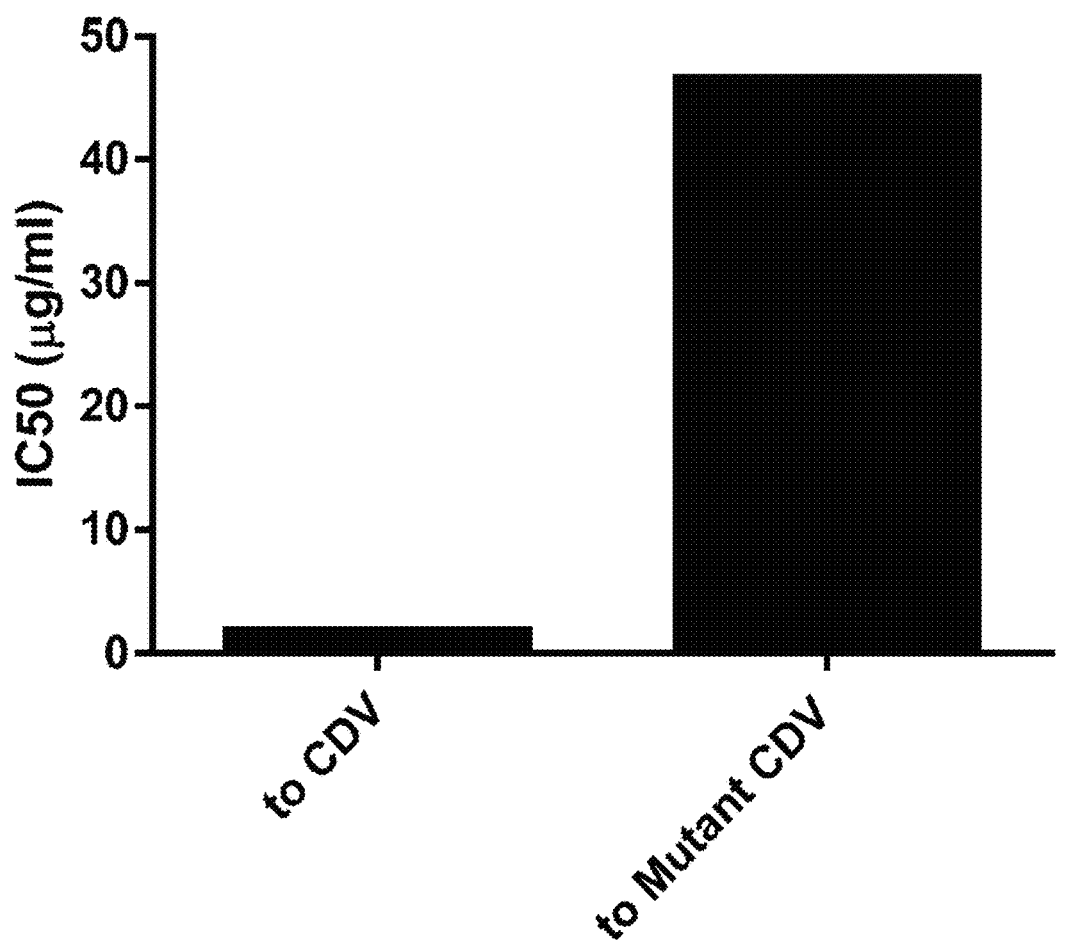

Y537D mutation in CDV H protein alters neutralizing antibody recognition in the receptor-binding region (FIG. 7).

The mutant CDV derived from human serum selection encodes 4 amino acid changes (1 in F, 1 in H, and 2 in L). The H mutation is expected to change binding to neutralizing antibodies.

The mouse monoclonal antibody 2F4 was used to confirm that the Y537D substitution altered antibody recognition in the receptor binding region. The 2F4 antibody is specific for the receptor binding region of MV H and is a potent neutralizer (Tahara, M., Ohno, S., Sakai, K., Ito, Y., Fukuhara, H., Komase, K., Brindley, M. A., Rota, P. A., Plemper, R. K., Maenaka, K., Takeda, M., 2013. The receptor-binding site of the measles virus hemagglutinin protein itself constitutes a conserved neutralizing epitope. Journal of virology 87, 3583-3586). Stock concentration of the 2F4 antibody used in this study was 1.85 mg/ml and its neutralizing activity against MV was confirmed. When the antibody was tested in CDV PRNT, the dilution causing 50% neutralization was determined to be 1,017 and the calculated 50% inhibitory concentration (IC50) was 1.8 µg/ml based on this dilution (FIG. 7). In contrast, the 2F4 antibody had relatively little inhibitory effect on infection with the CDV mutant as shown by the significantly lower PRNT value of 39.7, which was equivalent to IC50 of 46.6 µg/ml. These results indicated that the Y to D substitution diminished binding by antibody 2F4 in the receptor-binding region, suggesting that the amino acid substitution had a similar effect on antibodies responsible for neutralization activity in human serum.

The Y537D substitution alone causes resistance to human serum neutralization.

Figures 8A, 8B, 8C:
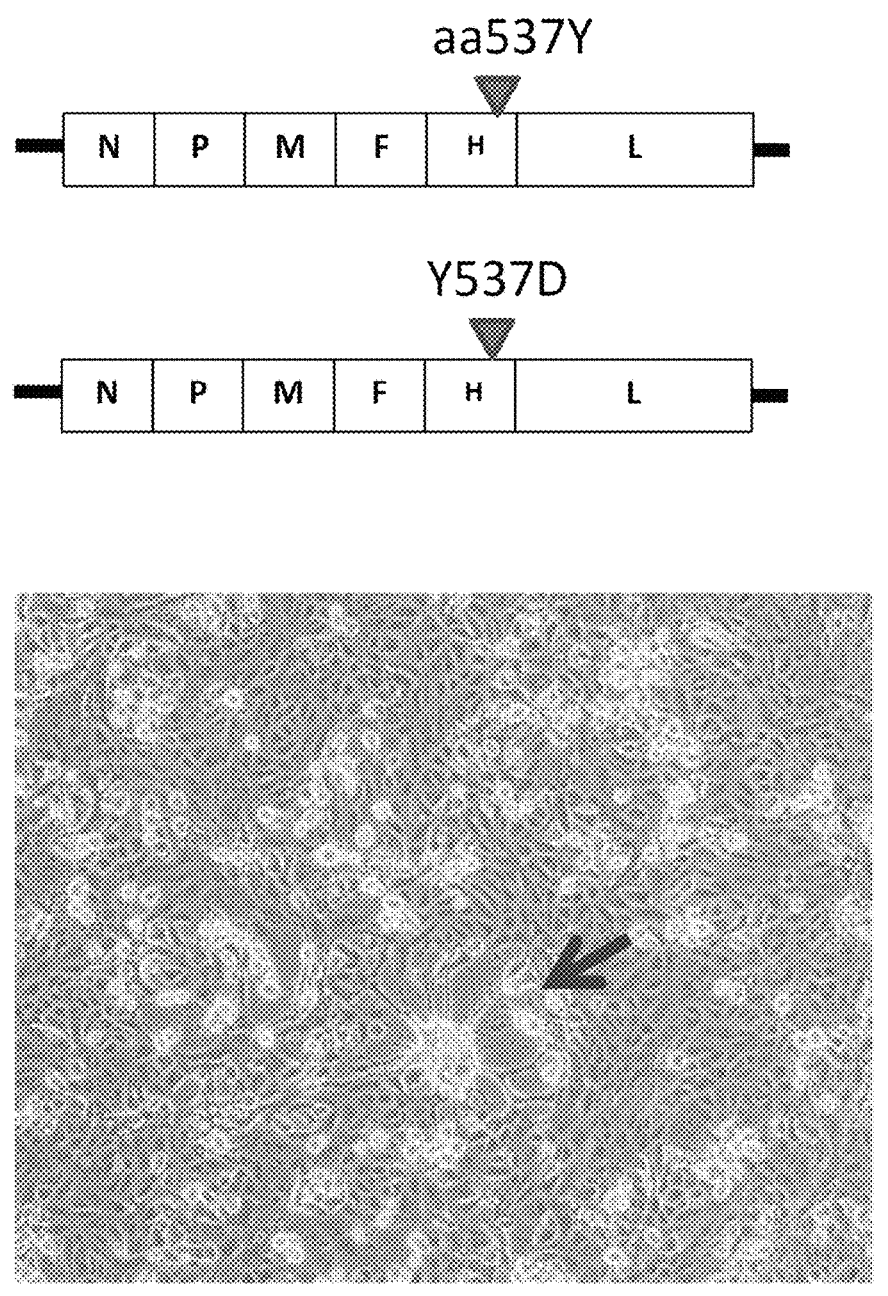
Figure 9:
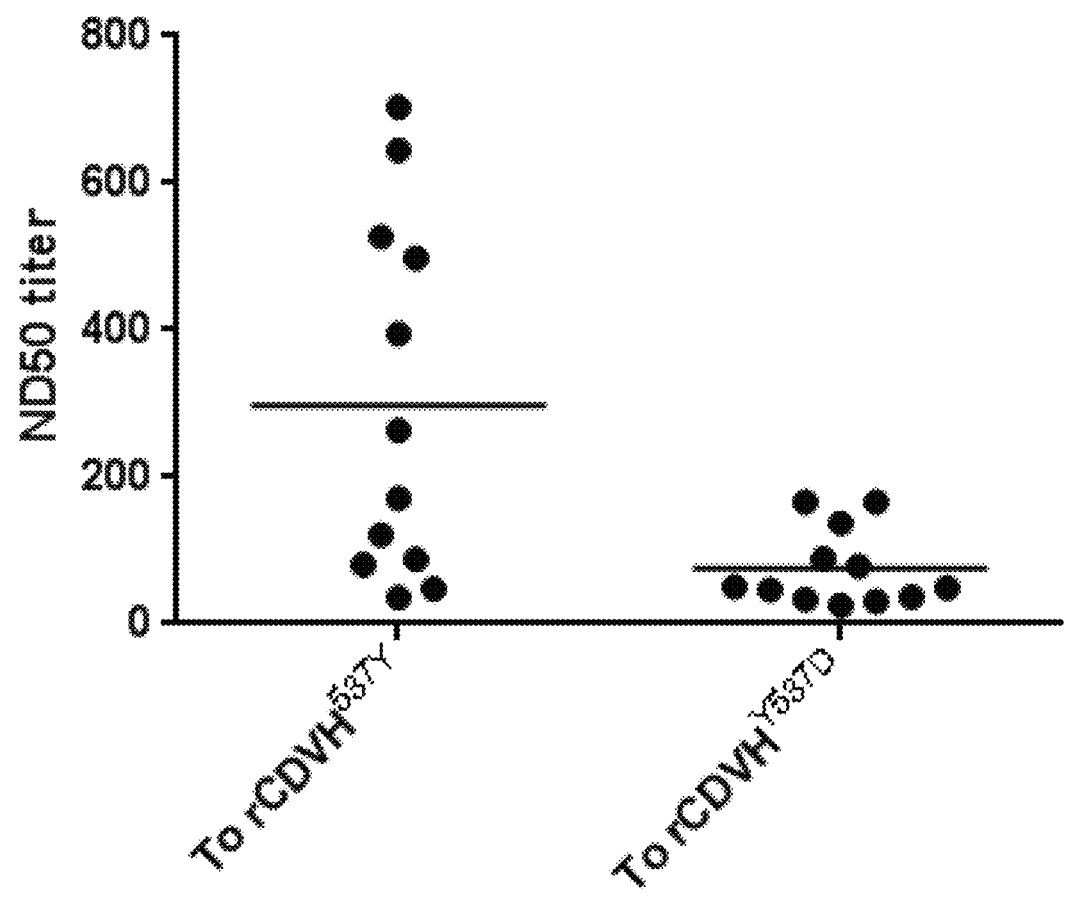

A recombinant CDV was rescued that only harbors the Y537D substitution (FIGS. 8A-8C). When compared with rCDVH$^{537Y}$ in PRNT, the rCDVH$^{Y537D}$ is less sensitive to the human serum neutralization (FIG. 9).

rCDVH$^{Y537D}$ propagated slightly better than rCDVH$^{537Y}$ on Vero and on transgenic Vero overexpressing dog SLAM receptor (FIG. 10), suggesting the Y to D mutation in H does not compromise the rCDVH$^{Y537D}$ cell entry and replication.

After rescue, the rCDVH$^{Y537D}$ virus was passaged on Vero cells 3 times after which nucleotide sequence of the H gene was analyzed. Results show that the D substitution is intact and no other mutations are present, suggesting the H gene is relatively stable during virus culture in Vero cells.

The invention is further described by the following numbered paragraphs:

1. A non-naturally occurring CDV neutralization-resistant mutant viral vector containing and expressing an exogenous nucleic acid.

2. The vector of paragraph 1, wherein the viral vector comprises a mutation in a CDV H protein.

3. The vector of paragraph 2, wherein the mutation is a Y537D substitution.

4. The vector of any one of paragraphs 1-3, wherein the viral vector comprises a mutation in a fusion (F) protein.

5. The vector of paragraph 4, wherein the mutation is a Y48S substitution.

6. The vector of any one of paragraphs 1-5, wherein the viral vector comprises a mutation in a large polymerase (L) protein.

7. The vector of any one of paragraphs 1-6, wherein the exogenous nucleic acid encodes a HIV immunogen.

8. A cell transfected with the vector of any one of paragraphs 1-7.

9. A method for eliciting an immune response against HIV comprising administering an effective amount of the vector of paragraph 7 or the cell of paragraph 8 to a mammal in need thereof.

10. The method of paragraph 9 further comprising administering an adjuvant.

11. The method of paragraph 10, wherein the adjuvant is comprised of an acrylic polymer and lecithin such as Adjuplex.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A non-naturally occurring CDV neutralization-resistant mutant viral vector containing and expressing an exogenous nucleic acid, wherein the vector encodes a polypeptide comprising a CDV H protein comprising a Y537D mutation in the CDV H protein, wherein position 537 corresponds to position 37 of SEQ ID NO:4.

2. The vector of claim 1, wherein the exogenous nucleic acid encodes a HIV immunogen.

3. A cell transfected with the vector of claim 1.

4. A method for eliciting an immune response against HIV comprising administering an effective amount of the vector of claim 2 to a mammal in need thereof.

5. The method of claim 4 further comprising administering an adjuvant.

6. The method of claim 5, wherein the adjuvant is comprised of an acrylic polymer and lecithin.

7. A method for eliciting an immune response against HIV comprising administering an effective amount of the cell of claim 3 to a mammal in need thereof.

8. The method of claim 7 further comprising administering an adjuvant.

9. The method of claim 8, wherein the adjuvant is comprised of an acrylic polymer and lecithin.

* * * * *

SEQUENCE LISTING

```
<160> NUMBER OF SEQ ID NOS: 9

<210> SEQ ID NO 1
<211> LENGTH: 50
<212> TYPE: PRT
<213> ORGANISM: Canine distemper virus

<400> SEQUENCE: 1

Met His Lys Gly Ile Pro Lys Ser Ser Lys Thr Gln Thr His Thr Gln
```

```
                1               5                  10                 15
            Gln Asp Arg Pro Pro Gln Pro Ser Thr Glu Pro Glu Glu Thr Arg Thr
                           20                  25                  30

Ser Arg Ala Arg His Ser Ile Thr Ser Ala Gln Arg Ser Thr His Tyr
                       35                  40                  45

Asp Pro
                50

<210> SEQ ID NO 2
<211> LENGTH: 50
<212> TYPE: PRT
<213> ORGANISM: Canine distemper virus

<400> SEQUENCE: 2

Met His Lys Gly Ile Pro Lys Ser Ser Lys Thr Gln Thr His Thr Gln
            1               5                  10                 15

Gln Asp Arg Pro Pro Gln Pro Ser Thr Glu Pro Glu Glu Thr Arg Thr
                           20                  25                  30

Ser Arg Ala Arg His Ser Ile Thr Ser Ala Gln Arg Ser Thr His Ser
                       35                  40                  45

Asp Pro
                50

<210> SEQ ID NO 3
<211> LENGTH: 47
<212> TYPE: PRT
<213> ORGANISM: Canine distemper virus

<400> SEQUENCE: 3

Asp Arg Asp Val Leu Ile Glu Ser Asn Leu Val Val Leu Pro Thr Gln
            1               5                  10                 15

Ser Phe Arg Tyr Val Ile Ala Thr Tyr Asp Ile Ser Arg Ser Asp His
                           20                  25                  30

Ala Ile Val Tyr Asp Val Tyr Asp Pro Ile Arg Thr Ile Ser Tyr
                       35                  40                  45

<210> SEQ ID NO 4
<211> LENGTH: 47
<212> TYPE: PRT
<213> ORGANISM: Canine distemper virus

<400> SEQUENCE: 4

Asp Arg Asp Val Leu Ile Glu Ser Asn Leu Val Val Leu Pro Thr Gln
            1               5                  10                 15

Ser Phe Arg Tyr Val Ile Ala Thr Tyr Asp Ile Ser Arg Ser Asp His
                           20                  25                  30

Ala Ile Val Tyr Tyr Val Tyr Asp Pro Ile Arg Thr Ile Ser Tyr
                       35                  40                  45

<210> SEQ ID NO 5
<211> LENGTH: 47
<212> TYPE: PRT
<213> ORGANISM: Measles virus

<400> SEQUENCE: 5

Asp Gly Asp Val Lys Leu Ser Ser Asn Leu Val Ile Leu Pro Gly Gln
            1               5                  10                 15

Asp Leu Gln Tyr Val Leu Ala Thr Tyr Asp Thr Ser Arg Val Glu His
                           20                  25                  30
```

```
Ala Val Val Tyr Tyr Val Tyr Ser Pro Ser Arg Ser Phe Ser Tyr
            35                  40                  45

<210> SEQ ID NO 6
<211> LENGTH: 47
<212> TYPE: PRT
<213> ORGANISM: Rinderpest virus

<400> SEQUENCE: 6

Asp Asp Asp Val Lys Leu Ser Ser Asn Leu Val Ile Leu Pro Ser Arg
1               5                   10                  15

Asn Leu Gln Tyr Val Ser Ala Thr Tyr Asp Thr Ser Arg Val Glu His
                20                  25                  30

Ala Ile Val Tyr Tyr Ile Tyr Ser Ala Gly Arg Leu Ser Ser Tyr
            35                  40                  45

<210> SEQ ID NO 7
<211> LENGTH: 47
<212> TYPE: PRT
<213> ORGANISM: Peste-des-petits-ruminants virus

<400> SEQUENCE: 7

Asp Asp Asp Ile Lys Ile Gly Ser Asn Met Val Ile Leu Pro Thr Met
1               5                   10                  15

Asp Leu Arg Tyr Ile Thr Ala Thr Tyr Asp Val Ser Arg Ser Glu His
                20                  25                  30

Ala Ile Val Tyr Tyr Ile Tyr Asp Thr Gly Arg Ser Ser Ser Tyr
            35                  40                  45

<210> SEQ ID NO 8
<211> LENGTH: 47
<212> TYPE: PRT
<213> ORGANISM: Dolphin morbillivirus

<400> SEQUENCE: 8

Asp Gln Asp Leu Lys Leu Glu Ser Asn Leu Val Val Leu Pro Thr Lys
1               5                   10                  15

Asp Phe Gly Tyr Val Thr Ala Thr Tyr Asp Thr Ser Arg Ser Glu His
                20                  25                  30

Ala Ile Val Tyr Tyr Val Tyr Asp Thr Ala Arg Ser Ser Ser Tyr
            35                  40                  45

<210> SEQ ID NO 9
<211> LENGTH: 47
<212> TYPE: PRT
<213> ORGANISM: Phocine distemper virus

<400> SEQUENCE: 9

Asp Asp Asp Val Leu Leu Glu Ser Asn Leu Val Val Leu Pro Thr Gln
1               5                   10                  15

Ser Phe Glu Tyr Val Val Ala Thr Tyr Asp Val Ser Arg Ser Asp His
                20                  25                  30

Ala Ile Val Tyr Tyr Val Tyr Asp Pro Ala Arg Thr Val Ser Tyr
            35                  40                  45
```